United States Patent [19]
Cohen et al.

[11] Patent Number: 4,563,461
[45] Date of Patent: Jan. 7, 1986

[54] SELECTIVE METHOD FOR BLOCKING 5HT$_2$ RECEPTORS

[75] Inventors: Marlene L. Cohen; Ray W. Fuller, both of Indianapolis, Ind.

[73] Assignee: Eli Lilly and Company, Indianapolis, Ind.

[21] Appl. No.: 473,882

[22] Filed: Mar. 10, 1983

[51] Int. Cl.$^4$ ............................................ A61K 31/44
[52] U.S. Cl. .................................................. 514/288
[58] Field of Search .......................... 424/261; 514/288

[56] References Cited

U.S. PATENT DOCUMENTS

| | | | |
|---|---|---|---|
| 3,113,133 | 12/1963 | Hofmann et al. | 260/285.5 |
| 3,228,941 | 1/1966 | Bernardi et al. | 260/285.5 |
| 3,249,617 | 5/1966 | Hofmann et al. | 260/285.5 |
| 3,580,916 | 5/1971 | Garbrecht | 546/69 |
| 4,230,859 | 10/1980 | Rucman | 546/69 |

FOREIGN PATENT DOCUMENTS

| | | | |
|---|---|---|---|
| 0003667 | 8/1979 | European Pat. Off. | 424/261 |
| 7216464 | 6/1973 | Netherlands | 424/261 |
| 1290203 | 9/1972 | United Kingdom | 424/261 |

OTHER PUBLICATIONS

Cohen et al., Chem. Abst. 100: 18298w, (1983).
Cassady et al., *J. of Med. Chem.*, vol. 17, No. 3, (Mar. 1974), pp. 300–307.
Goodman and Gilman, *The Pharmacologic Basis of Therapeutics*, (6th Ed. 1980), pp. 939–947.
Cecil, *Textbook of Medicine*, (15th Ed. 1979), pp. 731–732.
Cohen et al., *Hypertension*, 5, 676, (1983).
Berde, *The Medical Journal of Australia*, Special Supplement, Nov. 4, 1978, pp. 3–13.
Fanciullacci et al., *Headache*, 16, 226, (1976).
Calesnick, *AFP*, 25, 228, (1982).
Awouters, 5-Hydroxytryptamine in Perpheral Reactions, (Raven Press, N.Y., 1982), pp. 71–75.
Aellig, *Eur. J. Clin. Pharm.*, 25, 759, (1983).
Sulman et al., *Headache*, 17, 203, (1979).
Amano et al., ibid, 22, 249, (1982).
Cohen et al., *J.P.E.T.*, 227, 327, (1983).
Lance, *Brit. Med. J.*, 1970, (2), 327.
Friedman, *Headache*, 11, 148, (1972).
Saxena, ibid, 12, 44, (1972).
Lance and Anthony, *Proc. Aust. Assoc. Neurol.*, 7, 32, (1970).
Prusinski et al., *Pol. J. Pharmacol. Pharm.*, 37, Suppl. 189–193.

*Primary Examiner*—Stanley J. Friedman
*Assistant Examiner*—F. Abramson
*Attorney, Agent, or Firm*—James L. Rowe; Arthur R. Whale

[57] ABSTRACT

Method of blocking 5HT$_2$ without effect on alpha receptors with 1-loweralkyl-6-methyl-8β-(hydroxy)alkoxy carbonyl-5R-ergolines.

4 Claims, No Drawings

SELECTIVE METHOD FOR BLOCKING 5HT₂ RECEPTORS

This invention provides a method of blocking $5HT_2$ receptors without effect on alpha receptors which comprises administering to a mammal having an excess of serotonin centrally or peripherally a $5HT_2$ blocking dose of an ergoline of the formula:

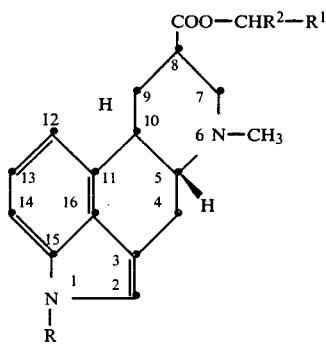

wherein R is $C_{1-3}$ alkyl or allyl, $R^1$ is $C_{1-3}$ hydroxyalkyl or $C_{1-3}$ dihydroxyalkyl and $R^2$ is H or $CH_3$, or a pharmaceutically acceptable salt thereof which dose does not affect alpha receptors.

Groups which R represents include methyl, ethyl, allyl, n-propyl and isopropyl. Illustrative of the groups which $R^1$ represents are hydroxymethyl, 1,2-dihydroxyethyl, 2-hydroxyethyl, 2-hydroxypropyl, 1,2-dihydroxypropyl, 1-hydroxyethyl, 2-hydroxyethyl, 1-hydroxypropyl, 1-methyl-2-hydroxyethyl and the like.

Pharmaceutically-acceptable acid addition salts of the compounds of formula I include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioxate, hexyne-1,6-dioate, benzoate, chlorobenzoate, methoxybenzoate, phthalate, terephthalate, benzenesulfonate, toluenesulfonate, chlorobenzenesulfonate, xylenesulfonate, phenylacetate, phenylpropionate, phenyl-butyrate, citrate, lactate, β-hydroxybutyrate, glycollate, malate, tartrate, methanesulfonate, propanesulfonate, naphthalene-1-sulfonate, naphthalene-2-sulfonate and the like salts.

Compounds illustrative of the above formula I include:

1,6-dimethyl-8β-(2-hydroxy)ethoxycarbonyl-5R-ergoline maleate 1-isopropyl-6-methyl-8β-(3-hydroxy)propoxy carbonyl-5R-ergoline succinate 1-ethyl-6-methyl-8β-(2-hydroxy-1-methyl)propoxycarbonyl-5R-ergoline hydrochloride 1-n-propyl-6-methyl-8β-(2,3-dihydroxy)propoxycarbonyl-5R-ergoline sulfate 1-isopropyl-6-methyl-8β-(2-hydroxy-1-methyl)ethoxycarbonyl-5R-ergoline hydrobromide and the like.

The preparation of compounds represented by formula I above is detailed in U.S. Pat. No. 3,580,916, issued May 25, 1971.

The novel method of this invention whereby $5HT_2$ receptors are blocked but alpha receptors are not affected at a given dose level is potentially useful in treating disease states in which an excess of circulating serotonin is a major cause. These disease states include hypertension, anorexia nervosa, depression, mania, carcinoid syndrome, migraine and vasospasm. The lack of alpha receptor inhibitory activity indicates that the usual undesirable side effects associated with alpha receptor blockade—postural hypotension, tachycardia, impotence, and increased plasma renin levels—will not accompany the use of a compound according to formula I in treating hypertension, etc. in contrast to many presently available hypotensive agents including ketanserin.

Compounds according to formula I have an extremely high affinity for $5HT_2$ receptors, with a much lower affinity for alpha receptors. Ratios of relative dissociation constants for interaction with alpha to $5HT_2$ receptors are of the order of 200,000–300,000 indicating dramatic selectivity for $5HT_2$ receptors. The apparent dissociation constants ($K_B$) are a measure of affinity for $5HT_2$ and alpha receptors and are expressed as the negative logarithm and are determined according to the following protocol.

Male Wistar rats (150–300 gram weight) were killed and their external jugular veins and thoracic aortas dissected free of connective tissue, cannulated in situ and placed in a modified Krebs' bicarbonate buffer in a suitable tissue bath. Two L-shaped 30-gauge stainless-steel hypodermic needles were inserted in each cannula and the dissected vessels gently pushed onto the needles. One needle was attached with thread to a stationary glass rod and the other to the transducer. [The procedure employed was that described by Hooker, Calkins and Fleisch, *Blood Vessels*, 14, 1, (1977) for use with circular smooth muscle preparations.]

The modified Krebs' bicarbonate buffer had the following makeup: (concentrations in millimoles): sodium chloride, 118.2; potassium chloride, 4.6; calcium chloride dihydrate, 1.6; potassium dihydrogenphosphate, 1.2; magnesium sulfate, 1.2; dextrose, 10.0; sodium bicarbonate, 24.8; and water q.s. to 1000 g. The tissue baths were maintained at 37° C. and were aerated with 95% oxygen-5% $CO_2$. An initial optimum resting force of 1 and 4 g. was applied to the jugular vein and aorta, respectively. Isometric contractions were recorded as changes in grams of force on a Beckman Dynograph with Statham UC-3 transducers and microscale accessory attachment. Tissues were allowed to equilibrate 1 to 2 hours before exposure to drugs. Control responses to serotonin in the jugular vein and to norepinephrine in the aorta were obtained. The vessels were then incubated with appropriate concentrations of antagonist for one hour. Responses to serotonin or to norepinephrine were then repeated in the presence of the antagonist. Contraction to serotonin was evaluated in the jugular vein since this tissue produces marked responses to serotonin in the absence of alpha receptors—see Cohen and Wiley, *J. Pharm. Exp. Ther.*, 205, 400 (1978). Alpha receptor antagonist activity was evaluated in the aorta.

Apparent antagonist dissociation constants were determined for each concentration of antagonist according to the following equation:

$$K_B = \frac{[B]}{[\text{dose ratio} - 1]}$$

wherein [B] is the concentration of the antagonist and the dose ratio is the ED$_{50}$ of the agonist in the presence of the antagonist divided by the control ED$_{50}$. These results are then expressed as the negative logarithm of K$_B$. The $-\log$ K$_B$ values obtained for 1-isopropyl-6-methyl-8β-(1-methyl-2-hydroxy)propoxycarbonyl-5R-ergoline and representative serotonin antagonists presently being marketed against 5HT$_2$ receptors and alpha adrenergic receptors are given below in Table 1. The table also gives the K$_B$ alpha/K$_B$ 5HT$_2$ ratios for each of the compounds.

TABLE 1

Apparent Dissociation Constants of Antagonists for 5HT$_2$ and alpha receptors determined in the rat jugular vein and aorta, respectively.

| Compound | 5HT$_2$ $-\log$ K$_B$ ± S.E. | alpha $-\log$ K$_B$ ± S.E. | Ratio K$_B$ alpha K$_B$ 5HT$_2$ |
|---|---|---|---|
| Spiperone | 10.1 ± 0.09 (8) | 10.0 ± 0.09 (13) | 13 |
| Ketanserin | 9.7 ± 0.07 (12) | 7.9 ± 0.04 (7) | 63 |
| Mianserin | 9.3 ± 0.09 (14) | 7.8 ± 0.07 (6) | 32 |
| Trazodone | 8.7 ± 0.09 (11) | 6.8 ± 0.12 (9) | 79 |
| Mepiprazole | 7.9 ± 0.09 (6) | 8.3 ± 0.13 (13) | 0.4 |
| Benzoctamine | 7.8 ± 0.08 (6) | 6.6 ± 0.08 (13) | 16 |
| 1-isopropyl-6-methyl-8β-(1-methyl-2-hydroxy)propoxy carbonyl-5R-ergoline | 10.27 ± 0.17 | 4.86 ± 0.13 | 300,000 |

The lack of alpha blocking activity for compounds of formula I was demonstrated by the following experiment. The in vitro rat aorta preparation described above was used. ED$_{50}$ (median effective dose) for norepinephrine was determined in the presence of a 10$^{-5}$ molar dose of the test compound and this ED$_{50}$ compared to a control ED$_{50}$. The resulting dose ratios are given in Table 2 below.

TABLE 2

| Compound | Dose-Ratio |
|---|---|
| 1-isopropyl-6-methyl-8β-(1-methyl-2-hydroxy)propoxycarbonyl-5R-ergoline | 3.6 |
| 1-allyl-6-methyl-8β-(2-hydroxy)ethoxycarbonyl-5R-ergoline | 2.4 |
| 2-ethyl-6-methyl-8β-(2,3-dihydroxy)-propoxycarbonyl-5R-ergoline | 4.1 |
| 1-isopropyl-6-methyl-8β-(2-hydroxy)-propoxycarbonyl-5R-ergoline | 1.0 |

None of the above compounds significantly antagonized alpha receptors at a 10$^{-5}$ M. dose.

In spontaneously hypertensive rats (SHR), in which blockade of alpha receptors but not 5HT$_2$ receptors lowers blood pressure, there was no effect upon intraperitoneal administration of 1-isopropyl-6-methyl-8β-(1-methyl-2-hydroxy)propoxycarbonyl-5R-ergoline at a 10 mg./kg. dose.

The relative potency and selectivity of one compound according to formula I, 1-isopropyl-6-methyl-8β-(1-methyl-2-hydroxy)propoxycarbonyl-5R-ergoline, for 5HT$_2$ and alpha receptors was demonstrated in vivo in pithed SHR according to the following protocol.

SHR were anesthesized with halothane, femoral arterial and venous catheters implanted as before and the trachea cannulated. Each rat was pithed by passing a steel rod through the right orbit and down the entire length of the spinal column. The steel rod remained in place for the duration of the experiment. Immediately after pithing, the rats were ventilated with room air via a rodent respirator which eliminated any anesthetic effects. An equilibration period of 15 minutes was observed prior to control measurements and administration of drugs or vehicle i.p. Increasing doses of serotonin or methoxamine were injected i.v. 15 minutes after the equilibration period. The response was recorded and the blood pressure allowed to recover to control levels. Methoxamine was used because it had a relatively specific alpha$_1$ receptor agonist action, and ketanserin selectively blocks alpha$_1$ receptors. The test drug was prepared fresh daily and administered by the intraperitoneal route. The compound shifted the serotonin response 22 and 480 fold at 0.1 and 3 mg./kg. dosages whereas at a 10 mg./kg. dose there was no shift in the response to methoxamine, an alpha agonist.

In humans and mammals other than SHR, hypertension may be mediated through 5HT$_2$ receptors. Thus, compounds of formula I would be expected to lower blood pressure in humans as does ketanserin, another 5HT$_2$ blocker, but without the side effects attributable to alpha adrenergic receptor blockade.

In carrying out our novel therapeutic process, a pharmaceutically-acceptable salt of a drug according to formula I above formed with a non-toxic acid is administered orally or parenterally to a mammal with an excess of circulatory serotonin in which it is desirable to block 5HT$_2$ receptors in order to alleviate symptoms attributable to excessive serotonin levels such as high blood pressure and migraines. For parenteral administration, a water soluble salt of the drug is dissolved in an isotonic salt solution and administered by the i.v. route. For oral administration, a pharmaceutically-acceptable salt of the drug is mixed with standard pharmaceutical excipients such as starch and loaded into capsules or made into tablets, each containing 0.1 to 100 mg. of active drug. Dosage levels of from 0.1–10 mg./kg. have been found to be effective in blocking 5HT$_2$ receptors. Thus, the oral dosage would be administered 2–4 times per day, giving a daily dosage range of about 0.003 to about 10.0 mg./kg. per day.

Other oral dosage forms, suspensions, elixirs and tablets, can also be utilized and are preparable by standard procedures.

We claim:

1. A method of blocking 5HT$_2$ receptors without effect on alpha receptors which comprises administering to a mammal having a peripheral excess of serotonin an 5HT$_2$ blocking dose of an ergoline of the formula:

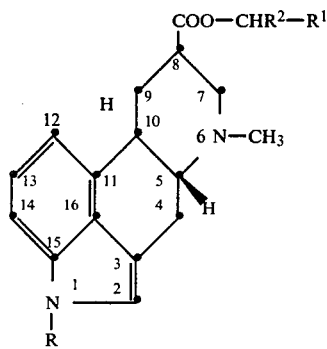

wherein R is $C_{1-3}$ alkyl or allyl, $R^1$ is $C_{1-3}$ hydroxyalkyl or $C_{1-3}$ dihydroxyalkyl and $R^2$ is H or $CH_3$, or a pharmaceutically acceptable salt thereof which dose does not affect alpha$_1$ receptors.

2. A method according to claim 1 in which said ergoline is 1-isopropyl-6-methyl-8β-(1-methyl-2-hydroxy)-propoxycarbonyl-5R-ergoline.

3. A method of treating migraine without encountering side effects attributable to alpha$_1$ receptor blockade which comprises administering to a mammal suffering from migraine a migraine relieving dose of an ergoline of the formula:

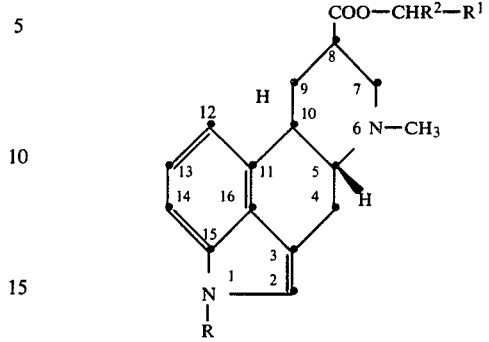

wherein R is $C_{1-3}$ alkyl or allyl, $R^1$ is $C_{1-3}$ hydroxyalkyl or $C_{1-3}$ dihydroxyalkyl and $R^2$ is H or $CH_3$, or a pharmaceutically acceptable salt thereof which dose does not affect alpha$_1$ receptors.

4. A method according to claim 3 in which said ergoline is 1-isopropyl-6-methyl-8β-(1-methyl-2-hydroxy)-propoxycarbonyl-5R-ergoline.

* * * * *

UNITED STATES PATENT AND TRADEMARK OFFICE
CERTIFICATE OF CORRECTION

PATENT NO. : 4,563,461

DATED : January 7, 1986

INVENTOR(S) : Marlene L. Cohen et al.

It is certified that error appears in the above—identified patent and that said Letters Patent is hereby corrected as shown below:

Column 4, line 66, "alpha" should read --$alpha_1$--.

Column 5, lines 3-15, the formula which reads

" 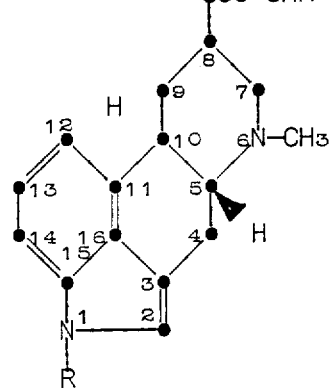 "    should read

-- 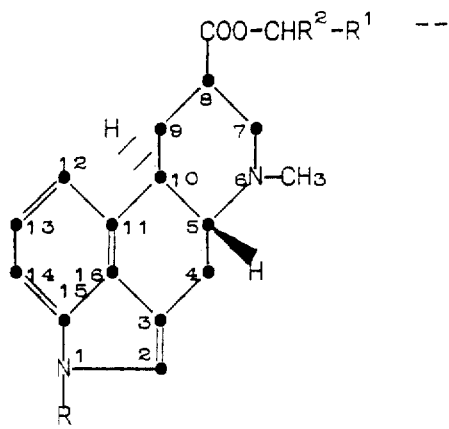 --

UNITED STATES PATENT AND TRADEMARK OFFICE
CERTIFICATE OF CORRECTION

PATENT NO. : 4,563,461  Page 2 of 2
DATED : January 7, 1986
INVENTOR(S) : Marlene L. Cohen et al.

It is certified that error appears in the above—identified patent and that said Letters Patent is hereby corrected as shown below:

Column 6, lines 5-17, the formula which reads

"[formula]"  should read

-- [formula] --.

Signed and Sealed this

Twenty-first Day of April, 1987

*Attest:*

DONALD J. QUIGG

*Attesting Officer*  *Commissioner of Patents and Trademarks*